United States Patent
Fujii et al.

(10) Patent No.: US 10,845,269 B2
(45) Date of Patent: Nov. 24, 2020

(54) LEAK DETECTION METHOD FOR OPEN EMISSION ANALYSIS, AND OPEN EMISSION ANALYSIS DEVICE

(71) Applicant: HONDA MOTOR CO., LTD., Tokyo (JP)

(72) Inventors: Satoshi Fujii, Aso (JP); Takuma Okonogi, Ozu-Machi (JP); Hideo Nihei, Tokyo (JP)

(73) Assignee: Honda Motor Co., Ltd., Tokyo (JP)

( * ) Notice: Subject to any disclaimer, the term of this patent is extended or adjusted under 35 U.S.C. 154(b) by 175 days.

(21) Appl. No.: 16/083,188

(22) PCT Filed: Feb. 28, 2017

(86) PCT No.: PCT/JP2017/008019
§ 371 (c)(1),
(2) Date: Sep. 7, 2018

(87) PCT Pub. No.: WO2017/154687
PCT Pub. Date: Sep. 14, 2017

(65) Prior Publication Data
US 2019/0094110 A1 Mar. 28, 2019

(30) Foreign Application Priority Data
Mar. 9, 2016 (JP) .................. 2016-046373

(51) Int. Cl.
*G01M 15/10* (2006.01)
*G01M 15/02* (2006.01)
(Continued)

(52) U.S. Cl.
CPC ............... *G01M 15/02* (2013.01); *F01N 3/00* (2013.01); *G01M 3/002* (2013.01); *G01M 3/025* (2013.01);
(Continued)

(58) Field of Classification Search
CPC .. G01M 15/02; G01M 15/102; G01N 1/2252; G01N 2001/2255
(Continued)

(56) References Cited

U.S. PATENT DOCUMENTS 3,603,155 A * 9/1971 Morris ................ G01M 15/102
73/863.01
3,699,814 A * 10/1972 Kaufman ................ G01N 1/24
73/863.11
(Continued)

FOREIGN PATENT DOCUMENTS

JP    S56-164949 A    12/1981
JP    S58-162828 A    9/1983
(Continued)

OTHER PUBLICATIONS

Extended European search report, dated Feb. 21, 2019, issued in the corresponding EP Patent Application 17763027.4.
(Continued)

*Primary Examiner* — Eric S. McCall
(74) *Attorney, Agent, or Firm* — Carrier Blackman & Associates, P.C.; William D. Blackman; Joseph P. Carrier (57) ABSTRACT

Exhaust gas discharged from an exhaust port is taken into an exhaust gas sampling unit together with the surrounding outside air. A leak detection mechanism, which detects the leakage of exhaust gas from a sampling port, includes a temperature sensor including an outside and an inside temperature sensors, and a temperature measuring instrument for measuring a temperature difference between inside and outside temperatures detected by the temperature sensor. A plurality of inside/outside paired temperature sensors is disposed in the circumferential direction of the sampling port. When a leak occurs, the temperature of the inside temperature sensors rises and the temperature difference between the inside and the outer and outside temperature
(Continued)

sensors increases, and the temperature measuring instrument detects the leak. When a leak occurs in a portion of the circumferential direction, only the temperature difference of the portion where the leak occurs is increased, and the location of the leak is identified.

10 Claims, 8 Drawing Sheets

(51) Int. Cl.
    *G01M 3/00*     (2006.01)
    *F01N 3/00*     (2006.01)
    *G01N 1/00*     (2006.01)
    *G01N 1/22*     (2006.01)
    *G01N 1/38*     (2006.01)
    *G01M 3/22*     (2006.01)
    *G01M 3/02*     (2006.01)
    *G01N 33/00*     (2006.01)

(52) U.S. Cl.
    CPC ............ *G01M 3/22* (2013.01); *G01M 15/102* (2013.01); *G01N 1/00* (2013.01); *G01N 1/22* (2013.01); *G01N 1/2252* (2013.01); *G01N 1/38* (2013.01); *G01N 33/0018* (2013.01); *G01N 2001/2255* (2013.01)

(58) Field of Classification Search
    USPC .......... 73/40.7, 49.1, 114.69, 114.71, 114.73
    See application file for complete search history.

(56) References Cited

U.S. PATENT DOCUMENTS

| | | | | |
|---|---|---|---|---|
| 4,419,021 A | | 12/1983 | Terada et al. | |
| 4,747,297 A | * | 5/1988 | Okayama | G01N 33/0032<br>73/23.33 |
| 4,924,095 A | * | 5/1990 | Swanson, Jr. | G01N 21/3504<br>250/338.1 |
| 5,210,702 A | * | 5/1993 | Bishop | G01N 21/33<br>250/338.5 |
| 5,469,731 A | * | 11/1995 | Decker | G01M 15/102<br>73/23.31 |
| 5,489,777 A | * | 2/1996 | Stedman | G01J 5/602<br>250/338.5 |
| 6,085,582 A | * | 7/2000 | Tripathi | G01M 15/102<br>73/114.71 |
| 6,148,656 A | * | 11/2000 | Breton | G01M 15/106<br>73/23.31 |
| 6,176,125 B1 | * | 1/2001 | Hirano | G01F 1/704<br>73/114.69 |
| 6,387,706 B1 | | 5/2002 | Eden | |
| 2004/0064243 A1 | * | 4/2004 | Nakamura | G01N 33/0062<br>701/114 |
| 2009/0241653 A1 | * | 10/2009 | Wang | G01M 15/102<br>73/114.71 |
| 2009/0308135 A1 | * | 12/2009 | Reinshagen | G01K 7/26<br>73/23.2 |
| 2010/0158068 A1 | | 6/2010 | Monteiro | |
| 2013/0118229 A1 | * | 5/2013 | Okada | G01M 15/10<br>73/23.31 |
| 2014/0338426 A1 | * | 11/2014 | Noda | F01N 11/00<br>73/40 |
| 2014/0338540 A1 | * | 11/2014 | Yoshimura | G01M 15/108<br>96/413 |
| 2015/0107330 A1 | * | 4/2015 | Yokoyama | G01M 15/102<br>73/23.31 |
| 2016/0116373 A1 | * | 4/2016 | Otsuki | G01N 1/2252<br>73/23.31 |
| 2016/0215716 A1 | * | 7/2016 | Yamamoto | F02M 26/20 |
| 2019/0064035 A1 | * | 2/2019 | Ochiai | G01M 15/104 |
| 2019/0187030 A1 | * | 6/2019 | Takagi | G01M 15/102 |

FOREIGN PATENT DOCUMENTS

| | | |
|---|---|---|
| JP | S59-006748 U1 | 1/1984 |
| JP | H05-223658 A | 8/1993 |
| JP | 2002-071528 A | 3/2002 |
| JP | 2014-224784 A | 12/2014 |

OTHER PUBLICATIONS

PCT/ISA/210 from the International Application Publication of PCT/JP2017/008019 with the English translation thereof.

* cited by examiner

LEAK DETECTION METHOD FOR OPEN EMISSION ANALYSIS, AND OPEN EMISSION ANALYSIS DEVICE

FIELD

The present invention relates to a leak detection method in an open exhaust gas analysis (open emission analysis) device for analyzing component concentrations in the exhaust gas of a vehicle and an open emission analysis device.

BACKGROUND

When measuring a concentration of a substance contained in exhaust gas, an open emission analysis method in which one end of an exhaust gas sampling unit for collecting exhaust gas is opened, and the exhaust gas and ambient outside air are aspirated and collected together for concentration analysis, and a device of the same are known. The open emission analysis enables measurements of the concentration at a state that is close to the actual running state of the vehicle.

However, in the open emission analysis, it is necessary to take in the total amount of exhaust gas, and if leakage occurs, the measurement of exhaust gas cannot be performed accurately.

Therefore, an accurate leak detection method is required. Patent Literature 1 discloses a method for detecting such a leakage.

In this method, a plurality of sampling pipes is provided in the vicinity of the exhaust gas sampling port, with one end of which facing the exhaust gas sampling port, and the other end of the respective sampling pipes being bundled to be a single tube and connected to a concentration analyzing device. The concentration analysis device performs the concentration analysis of a specific component of the exhaust gas, and if there is a leak, this component is detected.

CITATION LIST

Patent Literature

Japanese Unexamined Patent Application, Publication No. 2014-224784

BRIEF SUMMARY

Technical Problem

According to the above-described method of Patent Literature 1, since a plurality of sampling pipes has to be piped around the exhaust gas sampling unit, the piping becomes troublesome and the device becomes complicated and large, and therefore making it difficult to implement modifications when trying to change the number of sampling pipes or the sampling locations.

In addition, the device has become complicated and expensive due to continuously performing the concentration analysis of the sampled gas and the like. Also a certain amount of time is required for performing analysis which causes time lag to easily occur in the detection.

Moreover, even though there are a plurality of sampling locations, concentration analysis is performed on those gathered in one place, and therefore the location where leaks occur could not be identified. For this reason, attempts have been made to adjust the positional relationship between the discharge port of exhaust gas and the exhaust gas sampling port in order to eliminate this leakage, but it was difficult to achieve this adjustment, and repeated trial and error was necessary.

The present invention has been made in order to accomplish an objective of solving such problems.

Solution to Problem

In order to solve the above-described problem, a leak detection method for open emission analysis according to a first aspect thereof comprises taking in exhaust gas discharged from an exhaust port (7a) together with ambient outside air from an exhaust gas sampling unit (10), analyzing the collected exhaust gas, and, performing temperature measurement in the vicinity of a sampling port (11) of the exhaust gas sampling unit (10) to detect a leakage of exhaust gas from the sampling port (11).

The invention according to a second aspect thereof is characterized in that, in the above first aspect, the temperature measurement is performed at inside and outside positions of the sampling port (11) in the vicinity of the sampling port (11), and the leakage of exhaust gas is detected when a temperature difference between inside and outside temperatures exceeds a predetermined threshold value.

The invention according to a third aspect thereof is characterized in that, in the above first or second aspects, the temperature measurement is performed at a plurality of locations spaced apart from each other at a predetermined interval in the circumferential direction of the sampling port (11).

An open emission analyzing device according to a fourth aspect thereof comprises an exhaust gas sampling unit (10) for taking in exhaust gas discharged from an exhaust port (7a) together with ambient outside air, and a concentration analysis unit (30) for analyzing the sampled gas, wherein the exhaust gas sampling unit (10) has a sampling port (11) that is larger than the exhaust port (7a), and a temperature detecting unit (51) is arranged in the vicinity of the sampling port (11).

The invention according to a fifth aspect thereof is characterized in that, in the above fourth aspect, the temperature detecting unit includes an outside temperature detecting unit (51) for detecting a temperature on the outer peripheral surface of the exhaust gas sampling unit (10) and an inside temperature detecting unit (52) for detecting a temperature on the inner peripheral surface of the exhaust gas sampling unit (10), and that the temperature detecting unit further includes a temperature measuring unit (55) for detecting a temperature difference between the respective detected temperatures of the outside temperature detecting unit (51) and the inside temperature detecting unit (52).

The invention according to a sixth aspect thereof is characterized in that, in the above fifth aspect, the device includes a plurality of the temperature detecting units arranged at a plurality of locations spaced apart from each other by a predetermined interval in the circumferential direction of the sampling port.

The invention according to a seventh aspect thereof is characterized in that, in the above fifth or sixth, the exhaust gas sampling unit (10) is a hollow tubular member, and has an inner insertion tube (60) with a downstream side portion thereof being inserted to the exhaust gas sampling unit (10), and the inner insertion tube (60) is open at both ends thereof. This inner insertion tube (60) forms a gap with the inner peripheral surface of the exhaust gas sampling unit (10) to form a leakage passage (15) through which leaked exhaust gas passes and the temperature detecting unit (52) is disposed in the leakage passage (15) as well.

The invention according to an eighth aspect thereof is characterized in that, in the above seventh aspect, the inner insertion tube (60) has an upstream side portion extending upstream from the sampling port (11) of the exhaust gas sampling unit (10) and has an expanded portion (62a) which expands radially outward. The expanded portion (62a) has a distal end (61) that is located radially outward from the sampling port (11) and covers the upstream side of the leakage passage (15) as viewed in the axial direction.

The invention according to a ninth aspect thereof is characterized in that, in the above claim 7, the inner insertion tube (60A) in the gap has an upstream side portion extending upstream from the sampling port (11) of the exhaust gas sampling unit (10) and includes a curved portion (67) extending radially outwards so as to surround the edge portion of the sampling port (11) and provide a concave structure. An opening edge portion (14) of the sampling port (11) is located inside of the concave structure of the curved portion (67).

The invention according to a tenth aspect thereof is characterized in that, in any one of the above seventh through ninth aspects, the inner insertion tube (60) includes at least a portion that is made of a heat insulating material.

The invention according to an eleventh aspect thereof is characterized in that, in any one of the above seventh through tenth aspects, an upstream side opening of the inner insertion tube (60) is connected to the exhaust port (7a) via a filter (70) having air permeability.

The invention according to a twelfth aspect thereof is characterized in that, in the above eleventh aspect, the filter (70) is made of an elastic member.

Advantageous Effects

According to the invention of the first aspect, the temperature in the vicinity of the sampling port (11) is measured, and when the temperature becomes equal to or higher than the predetermined temperature, it is determined that exhaust gas has leaked from the sampling port (11), whereby leakage of the exhaust gas is detected. This method, compared to the method of analyzing a concentration, is more accurate as it is easier to detect and enables real-time detection. Moreover, a complicated and expensive device becomes unnecessary, and therefore allows simple, inexpensive and accurate detection to be performed.

According to the invention of the second aspect, the temperature is measured at the inside and outside positions in the vicinity of the sampling port (11), and the difference in temperature between the inside and outside is further measured. If the difference in temperature is equal to or less than the predetermined threshold value, then it is determined that exhaust gas has not leaked, whereas if the difference in temperature exceeds the predetermined threshold value, it is determined that exhaust gas has leaked. By using the temperature difference, the accuracy of detecting a leakage is further enhanced.

According to the invention of the third aspect, temperature measurement is performed at a plurality of locations spaced apart from each other by a predetermined interval in the circumferential direction of the sampling port (11), and therefore the presence or absence of leakage can be determined for each measuring location. Hence, when leakage occurs at a portion in the circumferential direction of the sampling port (11), the leaked place is easily identified and the adjustment to eliminate the leakage is facilitated.

According to the invention of the fourth aspect, in the open emission analysis device provided with the sampling port (11) larger than the exhaust port (7a), since the temperature detecting unit (51) is provided in the vicinity of the sampling port (11), the exhaust gas leakage from the sampling port (11) can be detected based on the change in temperature detected by the temperature detecting unit (51). In addition, compared to the method of analyzing a concentration, it is easier to detect the temperature difference, which enables real-time detection, and in turn accurate detection. Moreover, a complicated and expensive device becomes unnecessary, and thus a simple, inexpensive and accurate open emission analysis device can be realized.

According to the invention of the fifth aspect, the temperature detecting unit is constituted by a pair of the outside temperature detecting unit (51) and the inside temperature detecting unit (52), and the temperature measuring unit (55) measures the difference in temperature between the inside and the outside positions. Detecting the leakage base on this difference in temperature makes it possible to enhance the accuracy of leakage detection, and utilizing the outer temperature detecting unit (51), the inner temperature detecting unit (52), and the temperature measuring unit (55), which are relatively simple in structure and inexpensive, also realizes an open emission analysis device that is highly reliable, simple in structure and inexpensive.

According to the invention of the sixth aspect, the temperature detecting unit is plural and provided at a plurality of locations spaced apart from each other by a predetermined interval in the circumferential direction of the sampling port (11), and therefore it is possible to determine the presence or absence of leakage at each measuring location. Consequently, when leakage occurs at a portion in the circumferential direction of the sampling port (11), the place of leakage is easily identified and the adjustment to eliminate the leakage is facilitated. Therefore, an open emission analysis device can be realized which facilitates the adjustment of leakage elimination when leaking occurs.

According to the invention of the seventh aspect, the inner insertion tube (60) is provided, with the downstream side portion thereof being inserted inside the hollow portion of the exhaust gas sampling unit (10). A gap is formed between the inner insertion tube (60) and the inner peripheral surface of the exhaust gas sampling unit (10) to thereby form a leakage passage (15) through which any leaked exhaust gas passes, and the temperature detecting unit (52) is disposed inside the leakage passage (15) as well. Therefore, by separating the leakage passage (15) and the passage of the exhaust gas inside the leakage passage (15) with the inner insertion tube, it is possible to eliminate the influence of the temperature of the exhaust gas flowing in the inner insertion tube and to accurately measure the temperature of the leaking exhaust gas in the leakage passage (15). As a result, the accuracy of the leakage detection can be enhanced.

According to the invention of the eighth aspect, an upstream portion of the inner insertion tube (60) extending upstream from the sampling port (11) is an expanded portion (62a) expanding radially and outwardly. The expanded portion (62a) covers the upstream side of the leakage passage (15) as viewed in the axial direction, thereby making it less likely for a part of the traveling wind flowing on the outer peripheral surface side of the exhaust gas sampling unit (10) to enter the leakage passage (15). Therefore, measuring the temperature difference accurately can be realized.

According to the invention of the tenth aspect, since at least a part of the inner insertion tube (60) is made of a heat insulating material, it is possible to insulate the interior of the leakage passage (15) from the interior of the inner insertion tube and to reduce the influence due to the temperature of the exhaust gas flowing inside the intubation tube. Therefore, accurate temperature measurement can be realized.

According to the invention of the eleventh aspect, since the upstream side opening of the inner insertion tube (60) is connected to the exhaust port (7a) via the filter (70) having air permeability, the traveling wind around the exhaust port (7a) passes through the filter (70) and is taken into the exhaust gas sampling unit (10). Consequently, by suppressing the flow rate of the traveling wind taken into the exhaust gas sampling unit (10), the exhaust gas can be adjusted so as to prevent the leakage.

According to the invention of the twelfth aspect, the filter (70) is made of an elastic member, and therefore the filter (70) can be elastically deformed and brought into close contact with the muffler (6) and the sampling port (11) in the vicinity of the exhaust port (7a). Accordingly, it is easy to connect the filter (70) to the periphery of the exhaust port (7a) and the sampling port (11).

BRIEF DESCRIPTION OF DRAWINGS

FIGS. 4A-4B are views illustrating a principle of leakage detection; wherein

FIGS. 6A-6C are cross-sectional views of a part mainly composed of an exhaust gas sampling unit according to a second exemplary embodiment, wherein

FIGS. 8A-8B are diagrams explaining the effect of a filter, wherein

DETAILED DESCRIPTION

Hereinafter, a first exemplary embodiment relating to a leak detection method for open emission analysis and an open emission analysis device will be described with reference to FIGS. 1 to 4.

Figure 1:
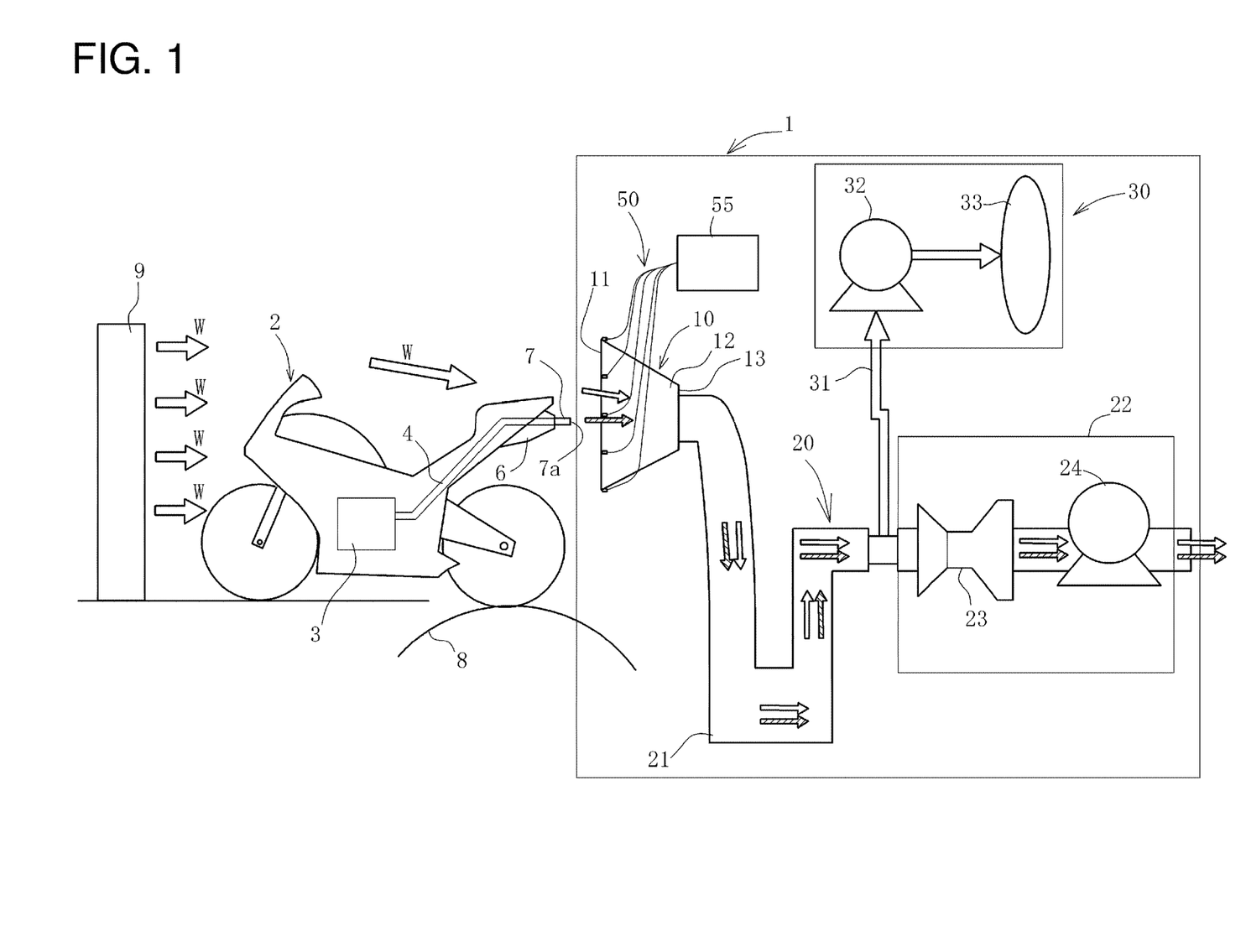
FIG. 1 is a diagram illustrating an open emission analysis system according to a first exemplary embodiment.

In FIG. 1, an open-type exhaust gas analysis system (open emission analysis system) 1 of the present exemplary embodiment includes an open-type exhaust gas sampling unit 10 for collecting exhaust gas discharged from the rear portion of a motorcycle 2 together with ambient outside air, a quantitative flow path 20 that is connected to the exhaust gas sampling unit 10 and through which the exhaust gas and the outside air sampled from the exhaust gas sampling unit 10 mix and flow, and a concentration analysis unit 30 for collecting a portion of the mixed gas in the quantitative flow path 20 and measuring the concentration.

The exhaust gas discharged from an engine 3 of the motorcycle 2 is sent to the rear of the vehicle through an exhaust pipe 4 and discharged to the rear via a muffler 6 and a tail pipe 7 projecting rearward from the rear end portion of the vehicle. The exhaust port 7a is located at the rear end portion of the tail pipe 7, etc. However, the provision of the tail pipe 7 is not always necessary and may be omitted. In this case, the rear end portion of the muffler 6 or the like serves as the exhaust port. Further, the muffler 6 may also be omitted, and in this case, the rear end portion of the exhaust pipe 4 serves as the exhaust port. Furthermore, the rear end portion of the exhaust pipe 4 may protrude from the rear end portion of the muffler, and this protruding portion may be used as the tail pipe 7.

The rear wheel of the motorcycle 2 is placed on a chassis dynamometer 8, and the rotation of the engine 3 can be changed in a predetermined running mode (emission mode). A blower 9 is disposed in front of the vehicle to blow wind W that travels towards the vehicle in proportion to the speed of the vehicle.

This traveling wind W flows toward the rear of the vehicle and is taken into the exhaust gas sampling unit 10 together with the exhaust gas.

The exhaust gas sampling unit 10 is provided substantially opposite to the exhaust port 7a and has an exhaust gas sampling port 11 that is larger than the exhaust port 7a. Between the exhaust port 7a and the sampling port 11, an outside air inflow gap (details will be described later) is provided.

In addition to taking in the exhaust gas discharged from the exhaust port 7a, the exhaust gas sampling unit 10 also takes in the traveling wind and the atmosphere (hereinafter referred to as outside air) around the exhaust port 7a from the outside air inflow gap.

A mixing section 21 for stirring and mixing the exhaust gas and the outside air, and a constant flow rate mechanism 22 for keeping the flow rate of the fluid flowing through the quantitative flow path 20 constant are provided in this order from the upstream side in the quantitative flow path 20.

The mixing section 21 includes a cyclone or the like to remove dusts, and stirs the exhaust gas and the outside air to be mixed to thereby produce a mixed gas obtained by diluting the exhaust gas with traveling wind. However, the mixing section 21 may be omitted.

The constant flow rate mechanism 22 regulates the flow rate so that the total flow rate of the mixed gas becomes constant, and includes a venturi 23 composed of a critical flow rate venturi and a suction blower 24 connected to a downstream portion of the venturi 23. The suction blower 24 is an example of a suction means for aspirating the gas inside the quantitative flow path 20 and the exhaust gas sampling unit 10.

The mixed gas in the quantitative flow path 20 is aspirated by the suction blower 24 to make the differential pressure between the upstream side and the downstream side of the venturi 23 equal to or higher than a predetermined value, thereby keeping the total flow rate of the mixed gas flowing through the quantitative flow path 20 constant. The mixed gas aspirated by the suction blower 24 is discharged to the outside.

It is to be noted that the constant flow rate mechanism is not limited to the above-described configuration, and various well-known devices such as a configuration including a critical orifice and a suction pump can be used for the mechanism. In addition, a variable flow rate control mechanism may be used instead of the constant flow rate mechanism.

A sampling line 31 for collecting a portion of the mixed gas flowing through the quantitative flow path 20 is connected between the mixing section 21 and the constant flow rate mechanism 22 in the quantitative flow path 20. An analyzer 33 for analyzing the mixed gas sampled from the sampling line 31 via the suction pump 32 is connected to the sampling line 31.

The analyzer 33 is, for example, a sampling bag for collecting the sampled mixed gas. The concentration of a predetermined component contained in the mixed gas collected in this collection bag is analyzed by a known analyzer such as NDIR, for example.

Figure 2:
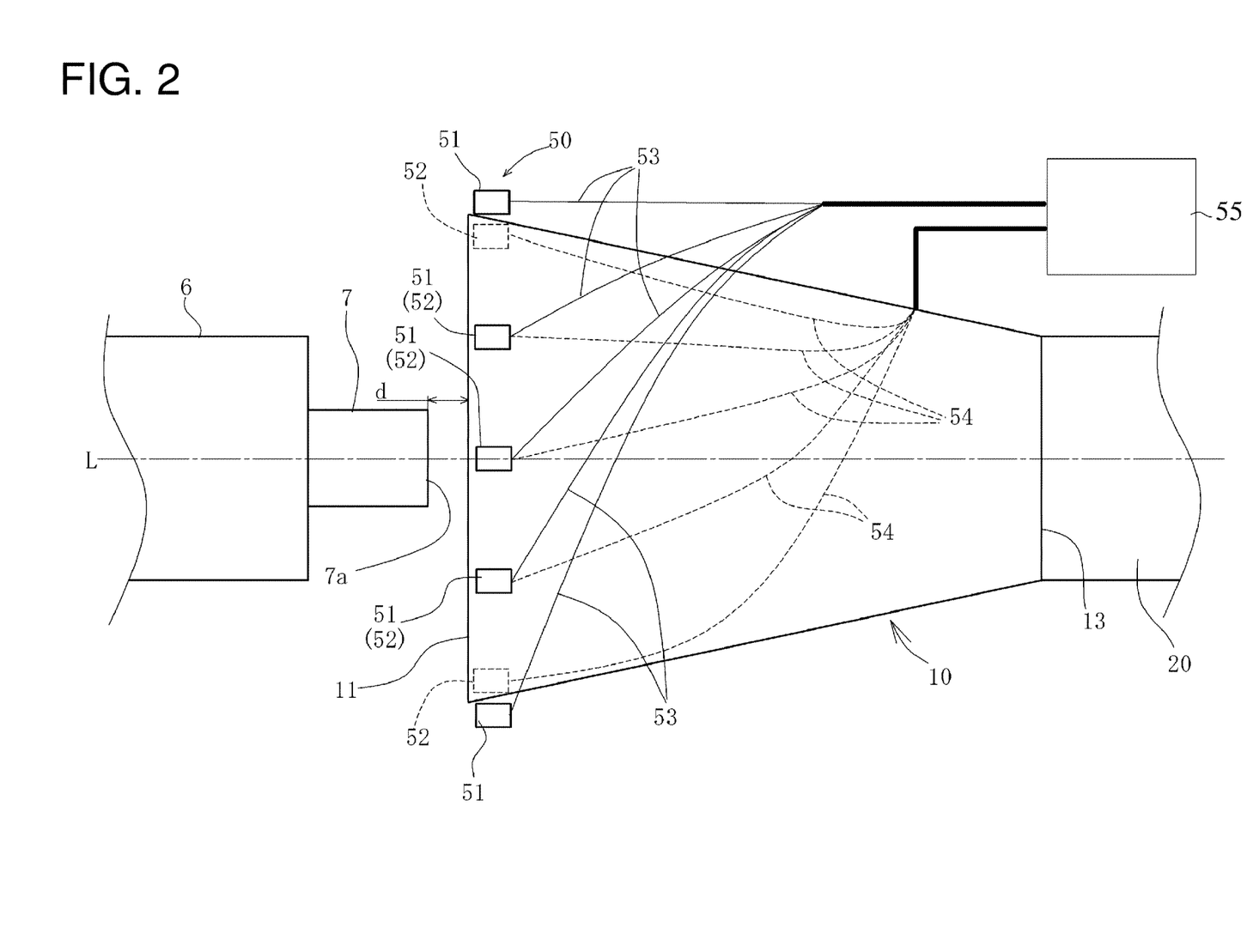
FIG. 2 is a side view of a part mainly composed of an exhaust gas sampling unit of the above-described system of the first exemplary embodiment.
Figure 3:
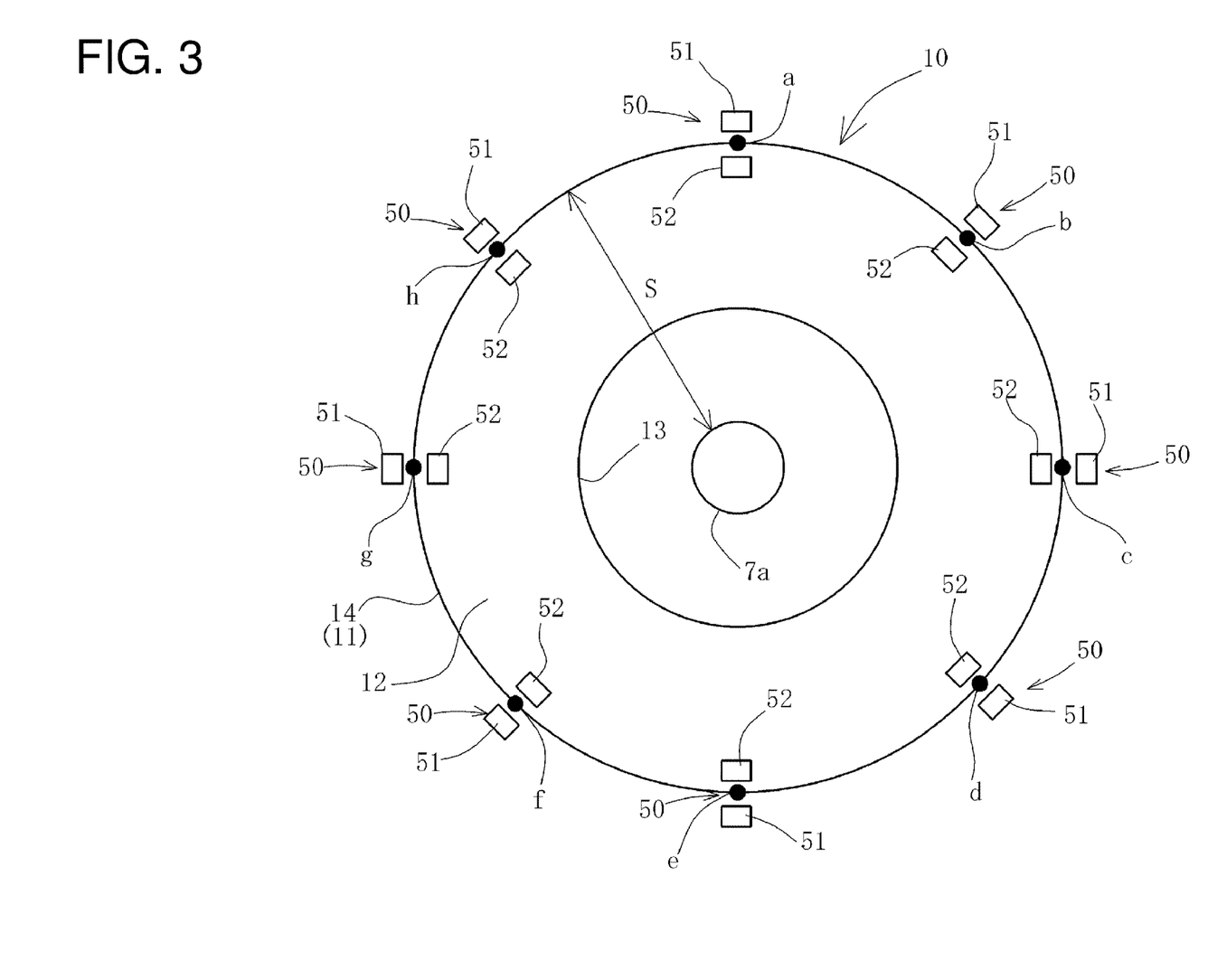
FIG. 3 is an axial view illustrating the exhaust gas sampling unit of FIG. 2.
Figure 4A:
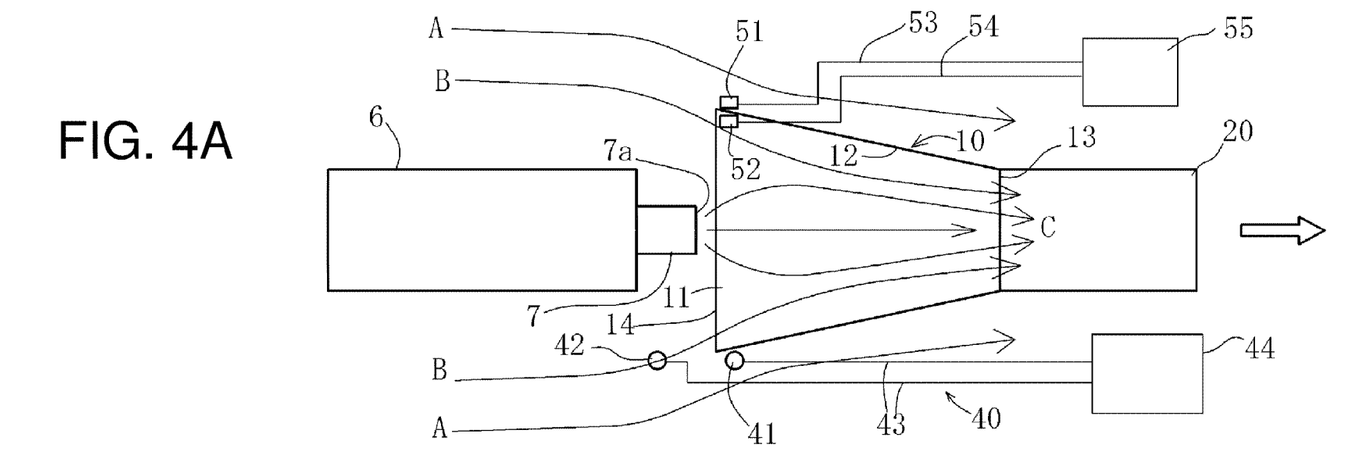
FIG. 4A shows a state where there is no leakage.
Figure 4B:
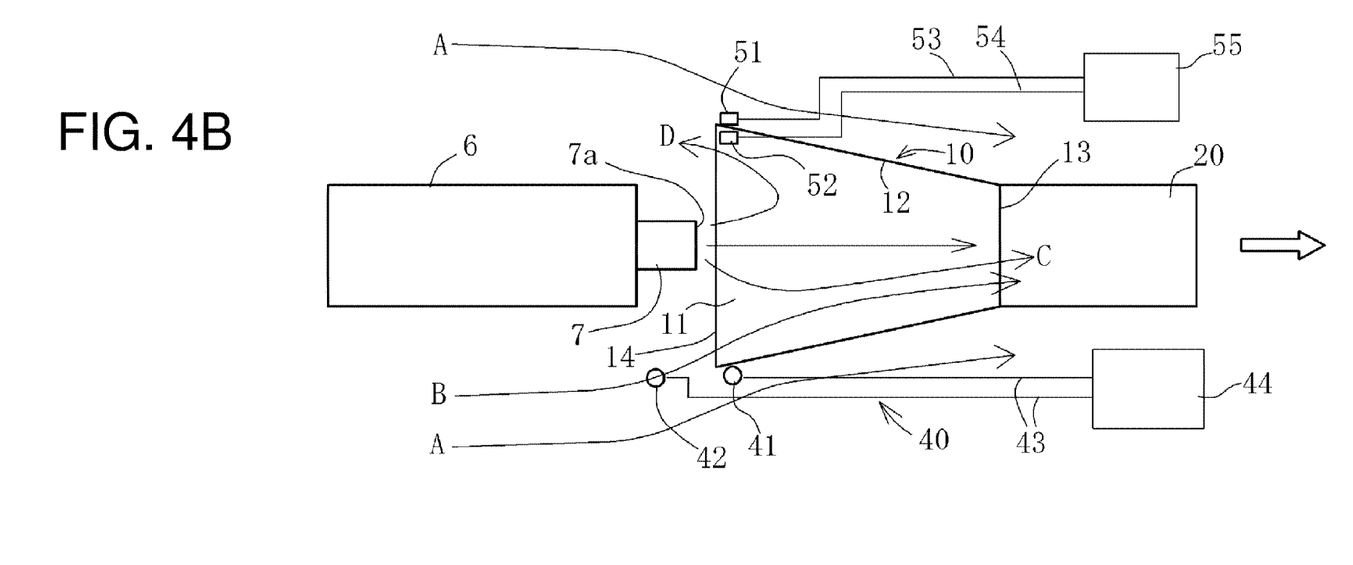
FIG. 4B shows a state where leakage occurs.

Further, as shown in FIGS. 2 to 4, a leak detection mechanism 50 for detecting the leakage of exhaust gas in the vicinity of the exhaust gas sampling port 11 is provided in the exhaust gas sampling unit 10.

Hereinafter, the exhaust gas sampling unit 10 and the leak detection mechanism 50 will be described in detail.

FIG. 2 shows a side view of the exhaust gas sampling unit 10 together with a respective part of the front and rear members. As shown in the figure, the exhaust gas sampling unit 10 is in the form of a cone having a tubular shape, opens with an enlarged diameter on the upstream side, and when viewed from the side, has a substantially truncated cone shape gradually decreasing in diameter from the upstream side to the downstream side and the side surface thereof is a tapered surface 12. The upstream end portion is the circular sampling port 11 which is a large diameter opening.

An upstream side end portion of the quantitative flow path 20 is connected to an opening 13 on the downstream side of the exhaust gas sampling unit 10. The exhaust gas sampling unit 10 has a passage cross sectional area that gradually decreases from the upstream side to the downstream side.

Note that the shape of the opening of the sampling port 11 and the opening 13 on the downstream side and the passage cross sectional shape of the exhaust gas sampling unit 10 are not limited to a circular shape, but that a polygonal shape such as a rectangular or triangular shape or an ellipse shape may be used.

In this embodiment, the exhaust port 7a is disposed on an axis L of the exhaust gas sampling unit 10 at a certain distance (indicated by "d" in FIG. 2) spaced apart upstream from the sampling port 11. However, the exhaust port 7a may be positioned anywhere and is not limited thereto but may be inserted into the exhaust gas sampling unit 10 through the sampling port 11, or may be disposed so as to overlap an opening edge portion 14 (refer to FIG. 3) of the sampling port 11 in the side view (FIG. 2).

FIG. 3 is an axial directional view (front view) showing the exhaust gas sampling portion 10 from the upstream side along the central axis L, and also shows the arrangement of the exhaust port 7a. As shown in this figure, the sampling port 11 and the opening 13 on the downstream side are concentric. Furthermore, if the tail pipe 7 is also cylindrical, then preferably it is disposed coaxially with the exhaust gas sampling unit 10, and the circular exhaust port 7a is also disposed substantially concentrically with respect to the sampling port 11 and the opening 13 on the downstream side.

The relationship between the diameters of the parts at this point is as follows: the sampling port 11>the opening 13 on the downstream side>the exhaust port 7a, wherein the diameter of the exhaust port 7a is the smallest and that of the sampling port 11 is the largest.

It is to be noted that the shape of the exhaust port 7a is, but not limited to a circular shape and various shapes may be adopted, for example, a polygonal shape such as a rectangular or triangular shape, or an ellipse shape, or the like.

A concentric gap exists at an interval of a distance S between the exhaust port 7a and the opening edge portion 14 of the sampling port 11. The gap in this axial directional view is herein referred to as an outside air inflow gap. The outside air around the exhaust port 7a flows through the outside air inflow gap into the sampling port 11.

Further, in this embodiment, the outside air inflow gap is concentric when viewed in the axial direction, but various shapes can be adopted according to the shapes of the exhaust port 7a and the sampling port 11.

As shown in FIGS. 2 to 4B, a leak detection mechanism 50 for detecting leakage of exhaust gas is provided in the vicinity of the sampling port 11 in the exhaust gas sampling unit 10. FIG. 4 is a view showing the principle of leak detection in which the flow of the exhaust gas and the outside air is described by taking the exhaust gas sampling unit 10 and the quantitative flow path 20 in FIG. 2 as a cross section. In the figure, FIG. 4A shows a state where there is no leakage whereas FIG. 4B shows a state where leakage occurs.

As shown in FIGS. 2 and 3, the leak detection mechanism 50 includes outside temperature sensors 51 disposed on the outer peripheral side of the sampling port 11 and inside temperature sensors 52 disposed on the inner peripheral side. As shown in FIG. 3, the sensors are arranged at equal intervals in the circumferential direction around the sampling port 11. For example, eight sensors are provided at intervals of 45°. Each mounting position of the sensors is denoted by the letters "a" to "h".

Each of the mounting positions "a" to "h" in FIG. 3 indicates the position around the sampling port 11, and the number is arbitrary as long as there is a plurality of them in the circumferential direction. However, the larger the number, the more accurate the measurement becomes possible.

There is a relatively high degree of freedom in the arrangement position of the exhaust gas sampling unit 10 in the front-rear direction. The state shown in FIG. 2 is an example of the mounting positions provided in the vicinity of the sampling port 11 which is the most upstream side end portion. With such a configuration in which the arrangement is in the vicinity of the opening edge portion 14 of the sampling port 11, error in measurement can be reduced.

Note that the range for arrangement of the inside temperature sensors 52 in the front-rear direction of the exhaust gas sampling unit 10 needs to be a range where the leaking exhaust gas is very likely to pass on the inner peripheral surface, and also a range that faces the leakage flow path of the exhaust gas as indicated by the arrow D in FIG. 4B.

Further, on the outer peripheral surface of the exhaust gas sampling unit 10, the arrangement range of the outside temperature sensors 51 in the front-rear direction of the exhaust gas sampling unit 10 needs to be reliably isolated from the inside temperature sensor 52 by the outer peripheral surface of the exhaust gas sampling unit 10, and also to face the traveling wind (indicated by the arrow A in FIG. 4A) flowing on the outer peripheral surface of the exhaust gas sampling unit 10.

The outer temperature sensors 51 and the inside temperature sensors 52 are composed of known thermocouples. However, various known temperature sensors can be appropriately used.

As shown in FIG. 2, each of the outside temperature sensors 51 is connected, by a signal line 53 wired around the exhaust gas sampling unit 10, to a temperature measuring instrument 55 disposed at a different location from the exhaust gas sampling unit 10.

Each of the inside temperature sensors 52 is also connected to the temperature measuring instrument 55 by a signal line 54 that is wired on the inner periphery of the exhaust gas sampling unit 10 and drawn out to the exterior of the exhaust gas sampling unit 10 at an appropriate position.

Each outer temperature sensor 51 and each inside temperature sensor 52 are paired on the inside and outside with the opening edge portion 14 of the sampling port 11 interposed therebetween. The temperature difference between each pair of the outside temperature sensor 51 and the inside temperature sensor 52 is continuously measured by the temperature measuring instrument 55.

Very little difference in temperature is observed between each pair of outer temperature sensor 51 and the inside temperature sensor 52 when there is no leakage of the exhaust gas; however, this difference in temperature increases as leakage occurs.

In addition, the temperature measuring instrument 55 measures with each pair of temperature sensors. For example, in this embodiment, the temperatures of each of the pairs from "a" to "h" are measured, and when leakage partially occurs, not in the entire circumference of the sampling port 11 but in a portion thereof, only the temperature difference of the portion where leakage occurred increases. With this configuration, confirmation can be promptly made as to where the leakage has occurred from among the locations of the pairs "a" to "h" (or the vicinity thereof) on the circumference of the sampling port 11.

Next, the principle of leakage detection base on temperature will be explained. As shown in FIG. 4A, if the flow rate of the quantitative flow path 20 is appropriate, the exhaust gas (arrow C) flowing out from the exhaust port 7a, together with the ambient traveling wind (arrow B), is taken in from the sampling port 11 into the exhaust gas sampling unit 10, flows to the quantitative flow path 20, and is subjected to concentration analysis by the concentration analysis unit 30.

At this time, the outside temperature sensor 51 and the inside temperature sensor 52 positioned near the opening edge portion 14 of the sampling port 11 face the traveling wind (arrow A) flowing on the outer peripheral surface of the exhaust gas sampling unit 10 and the traveling wind (arrow B) flowing on the inner peripheral surface thereof, respectively, (for the sake of convenience, only one pair of the temperature sensors is illustrated in FIG. 4A). In addition, the temperature of the outside air (arrow B) in the vicinity of the inside temperature sensor 52 is not affected by the leakage of the exhaust gas because there is no leakage of the exhaust gas, and thereby a difference in temperature with that of the traveling wind (arrow A) passing through the outside temperature sensor 51 is not big. Therefore, the difference in temperature is equal to or less than a preset threshold value and it can be concluded that there is no leakage. The threshold value is appropriately set by a prior test.

On the other hand, as shown in FIG. 4B, when the flow rate of the exhaust gas and the flow rate of the outside air to be taken in through the sampling port 11 are greater than the flow rate (suction flow rate) of the quantitative flow path 20, a portion of the exhaust gas bounces back, as indicated by arrow D, and leaks out from the sampling port 11.

Therefore, as the leaking exhaust gas passes in the vicinity of the inside temperature sensor 52, the temperature of the inside temperature sensor 52 rises. Meanwhile, since the outside temperature sensor 51 substantially maintains the temperature of the traveling wind indicated by the arrow A, a large difference in temperature occurs between the outside temperature sensor 51 and the inside temperature sensor 52. When this difference in temperature exceeds the threshold value, it can be determined that leakage has occurred, and therefore the leakage can be detected swiftly.

Figure 5:
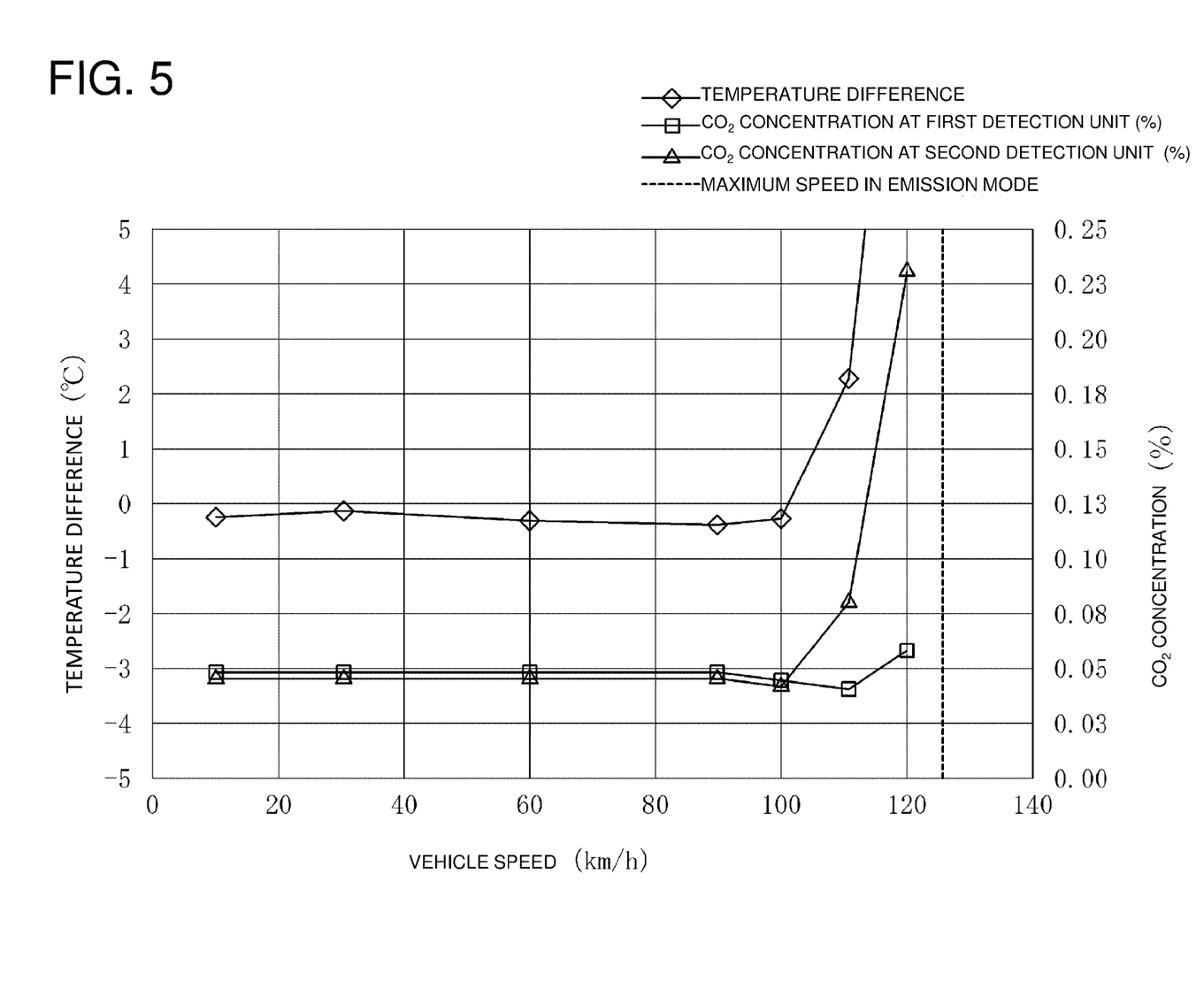
FIG. 5 is a graph showing leakage detection by temperature difference and concentration analysis.

FIG. 5 is a graph comparing the method of leakage detection based on the temperature difference of the present exemplary embodiment and the method of leak detection according to the conventional concentration detection. In this graph, the temperature difference (° C.) is shown on the left vertical axis, the concentration (%) of $CO_2$ on the right vertical axis, and the vehicle speed (km/h) on the horizontal axis.

The conventional method of leakage detection is for verifying the effectiveness of the leakage detection based on the temperature difference of the present application.

When the vehicle engine 3 is operated in a predetermined emission mode to change the vehicle speed, the difference in temperature is almost constant up to 100 km/h in the measurement of the present exemplary embodiment. In this situation under the assumption that the threshold value is 0, the measurement is equal to or less than the threshold value, indicating that leakage has not occurred.

The difference in temperature rapidly occurs and exceeds the threshold value when the vehicle speed slightly exceeds 100 km/h, thereby making it possible to detect the occurrence of leakage. Approximately 125 km/h is the maximum speed in the emission mode.

The measuring of concentration of $CO_2$ is performed by a known method to measure the concentration of $CO_2$, which is an example of a specific component in the exhaust gas, in the vicinity of the sampling port 11. In the method, it is determined that the leakage of exhaust gas has occurred when a concentration higher than a predetermined value is detected.

This concentration analysis is a conventional effective leak detection method. However, the component to be subjected to the concentration measurement is not limited to $CO_2$, and other components may be used.

Hereinafter, this concentration measurement will be described. As shown in FIGS. 4A and 4B, a concentration measuring unit 40 is provided for analyzing a specific exhaust gas component in the vicinity of the sampling port 11 and measuring its concentration. The concentration measuring unit 40 has a first detection unit 41 for collecting the outside air around the exhaust port 7a on the upstream side of the sampling port 11, and a second detection unit 42 for collecting the outside air at a position which is substantially the same as the temperature measurement position of the outside temperature sensors 51, the second detection unit 42 being located on the downstream side from the first detection unit 41. The outside air collected by each detection unit is sent to an analyzer 44 through a sampling tube 43.

Note that a plurality of the second detection units 42 is arranged so as to correspond to the number of outside temperature sensors 51, and a plurality of the first detection units 41 are also arranged corresponding to the number of second detection units.

The analyzer 44 continuously measures the concentration of a specific component (for example, $CO_2$) from the outside air sampled from each of the first detection units 41 and the second detection units 42. Although this concentration measuring unit 40 can be configured by known components, it can be configured in the same way as that described in Patent Literature 1.

As shown in the graph of FIG. 5, the concentrations of the specific component ($CO_2$) in the first detection unit 41 and the second detection unit 42 detected by the analyzer 44 are each lower than the threshold value (for example, 0.05%) in the speed range in which leakage does not occur, and both indicating a state of no leakage.

When the vehicle speed exceeds 100 km/h, there is leakage of exhaust gas. The exhaust gas leaks from the vicinity of the sampling port 11 and heads toward the second detection unit 42, and therefore the concentration of the specific component detected by the second detection unit 42 increases sharply, and the leakage is detected. At this time, the exhaust gas has barely reached the first detection unit 41 on the upstream side, leading to a delay in the concentration detection by the first detection unit 41.

As described above, it is understood that the leakage detection based on the temperature difference in the present exemplary embodiment is capable of realizing the same precision as that by the concentration measurement of the second detection unit 42.

Although the method and the configuration of the device for leakage detection are different between the one based on the temperature difference and the one based on the concentration measurement, in terms of leakage detection, both methods can perform detection with the same accuracy. However, when comparing the rise of the graph in a portion exceeding 100 km/h, it is understood that the detection based on the temperature difference of the present exemplary embodiment shows a slightly sharp change, and hence the detection accuracy is higher.

Next, an open emission analysis and a leakage detection method thereof of the present exemplary embodiment will be specifically described.

First, as shown in FIG. 1, after arranging the sampling port 11 of the exhaust gas sampling unit 10 at a predetermined position with respect to the exhaust port 7a, the engine 3 is started to operate in a predetermined emission mode. In correspondence with the operation of the engine 3, the blower fan 9 blows the traveling wind W for the vehicle speed toward the vehicle.

Therefore, when the suction blower 24 of the exhaust gas analysis system 1 is started, the exhaust gas discharged from the exhaust port 7a and the outside air around the exhaust port 7a are taken into the exhaust gas sampling unit 10 from the sampling port 11, and thereafter flow to the quantitative flow path 20 as a mixed gas.

At this time, if there is no leakage, as shown in FIG. 4A, the exhaust gas flows to the downstream side as indicated by arrow C and the entire amount is taken in. Part of the traveling wind W flows on the outer peripheral surface of the exhaust gas sampling unit 10 as indicated by arrow A and the other part flows as outside air on the inner peripheral surface of the exhaust gas sampling unit 10 as indicated by arrow B. Since the temperatures of the traveling wind and the outside air that are inside and outside the exhaust gas sampling unit 10 are substantially constant, the temperature differences between the respective detected temperatures of the outside temperature sensors 51 and the inside temperature sensors 52 detected by the temperature measuring instrument 55 are equal to or lower than the threshold value, and therefore it can be confirmed that leakage has not occurred.

On the other hand, when a leakage occurs, as shown in FIG. 4B, part of the exhaust gas bounces back as shown by an arrow D and flows toward the sampling port 11 thereby raising the temperature detected by the inside temperature sensors 52. Meanwhile, the temperature detected by the outside temperature sensors 51 does not change very much for it faces the traveling wind indicated by the arrow A flowing on the outer peripheral surface of the exhaust gas sampling unit 10. Therefore, the difference in temperature between the temperatures detected by the outside temperature sensor 51 and the inside temperature sensor 52 rapidly increases, and the temperature measuring instrument 55 determines that the leakage of exhaust gas has occurred when the temperature exceeds the threshold value, and thus the leakage can be detected. Moreover, the leakage can be detected in real time due to the fact that the temperature measuring instrument 55 performs analyzation continuously.

When the temperature measuring instrument 55 determines that exhaust gas is leaking, the leakage of the exhaust gas may be eliminated by, for example, adjusting the positional relationship between the exhaust port 7a and the sampling port 11. At this time, leak detection is performed for the temperature sensors forming each pair, that is, for each of the mounting positions "a" to "h" in FIG. 3, and therefore the location of where leakage occurred can be easily identified. Moreover, because the degree of leakage can also be found based on the magnitude of the temperature difference, the adjustments for eliminating the leakage is facilitated.

For example, if a leak occurs at position "c" which is close to the interior of the vehicle body and at position "e" which is the lower end portion, the temperature differences at the "c" and "e" positions exceeding the threshold value are detected by the temperature measuring instrument 55. This leakage may be eliminated by appropriately adjusting the intervals between the exhaust port 7a and the sampling port 11 at the positions "c" and "e".

At this time, in FIG. 3, the position of the exhaust port 7a is moved relatively in the radial direction for adjustment, but if the interval between a certain location (for example, d) is shortened, the interval between the other locations (for example, h) is widened, which causes a new leak to occur from that point. In order to achieve an adjustment having optimum positions wherein as a whole there is no leakage, it may be necessary to perform adjustments with repeated trial and error.

However, even in such a case, in the present exemplary embodiment, the temperature difference of each part can be identified in every adjustment, and therefore making adjustments for optimum position is facilitated through a small number of trials with reference to this detection result, and it is possible to speed up this kind of troublesome adjusting task.

Besides, in order to detect the leakage by measuring the temperature differences, temperature sensors of a type having a relatively inexpensive and simple structure such as a thermocouple can be used. Further, the connection between the temperature sensors and the temperature measuring instrument 55 can also be connected by signal lines 53 and 54 which are relatively thin and bendable and easily handled. The provision of a large number of sampling pipes that are bulky and difficult to handle as in the conventional example is not necessary, and thus the structure is simplified and easy to assemble.

Moreover, unlike the conventional example in which the complicated and expensive analyzer 44 performs continuous component analysis while concentration analysis using infrared rays or the like is performed, continuous real-time measurement of the temperature differences performed by the temperature measuring instrument 55 is easy, and the temperature measuring instrument 55 itself is simple and inexpensive. Besides, although a single device of the temperature measuring instrument 55 is capable of processing each of the plurality of temperature sensors, if concentration analysis is to be carried out for each detection unit in the conventional example, then it is necessary to provide as many expensive analyzers 44 as there are detection units, which is not practical.

Therefore, according to the device of the present exemplary embodiment, on the whole, the structure is simple, inexpensive, easy and capable of accurately measuring a location where a leakage has occurred.

Next, a second exemplary embodiment will be described.

Figure 6A:
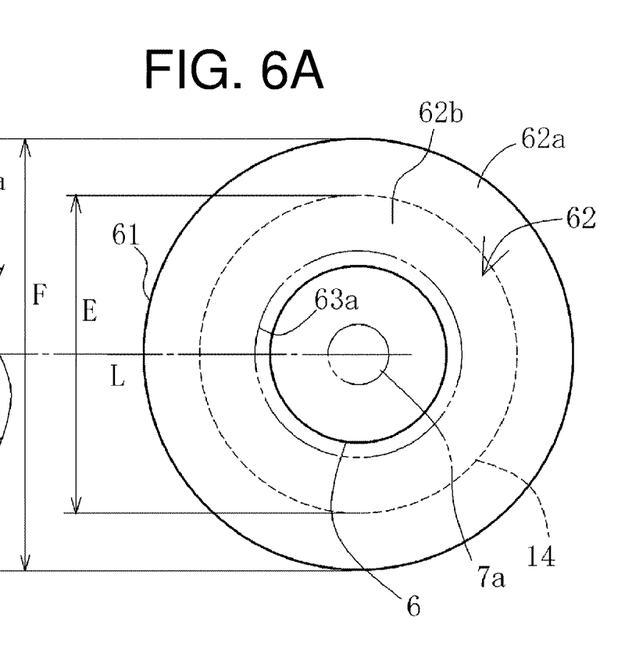
FIG. 6A shows an outer diameter of the opening being larger than that of the exhaust port.
Figures 6B, 6C:
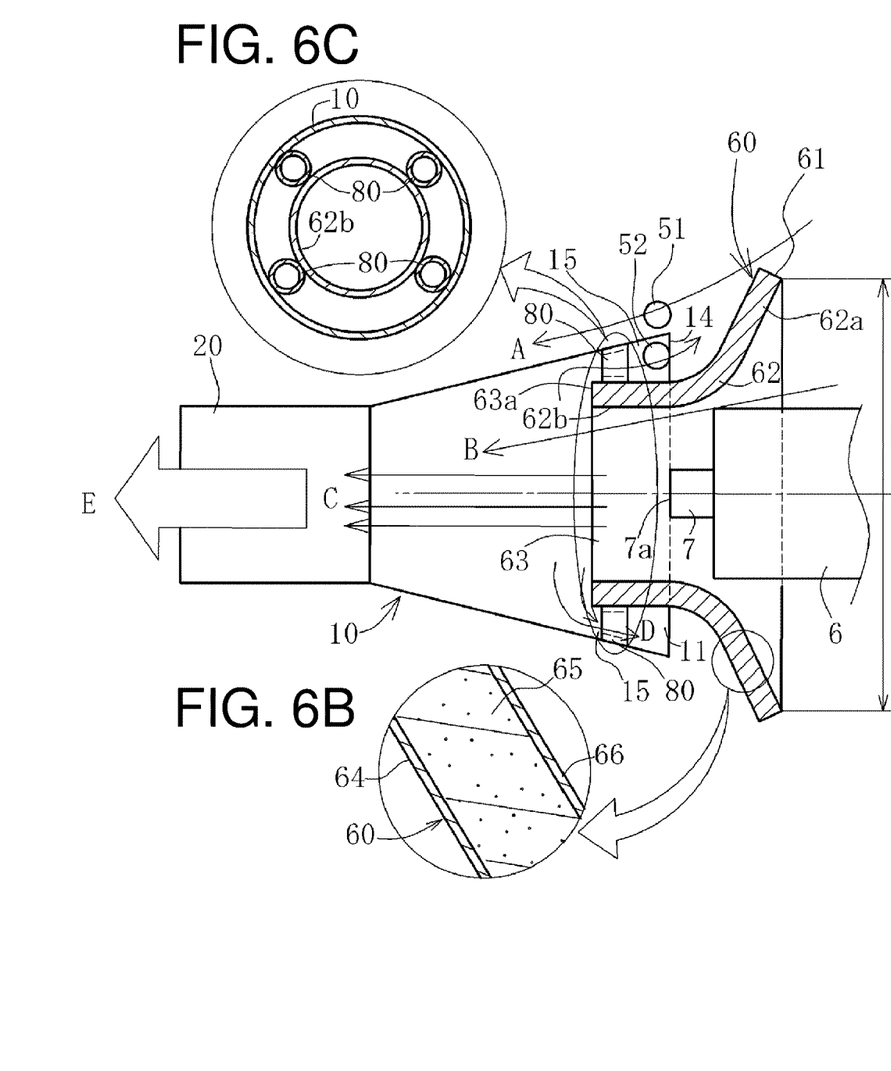
FIG. 6B shows an enlarged cross-sectional view of the material of the thermal insulating funnel.
FIG. 6C shows a cross section perpendicular to the axis of the exhaust gas sampling unit.

FIGS. 6A-6C are cross-sectional views, similar to FIG. 4A, in which a thermal insulating funnel 60 is disposed on the inner side portion of the sampling port 11 of the exhaust gas sampling unit 10 of the first exemplary embodiment. The thermal insulating funnel 60 is a tubular member made of a heat insulating material and corresponds to the inner insertion pipe of the present invention. The upstream side end portion of the thermal insulating funnel 60 forms a large diameter opening 61, and a diameter F thereof is larger than a diameter E of the opening edge portion 14 of the sampling port 11.

An upstream side portion of an intermediate portion 62 extends upstream from the sampling port 11 to form an expanded portion 62a which expands radially outward. The distal end of the expanded portion 62a forms the large diameter opening 61. The large diameter opening 61 has an edge portion located radially outward from the edge portion of the sampling port 11, and when viewed from the upstream side in the axial direction, the expanded portion 62a covers the opening edge portion 14 of the sampling port 11. The downstream side portion of the intermediate portion 62 forms a small diameter portion, and the downstream side end portion forms a smallest-diameter opening 63. However, an outer diameter of an edge portion 63a of the opening 63 is larger than that of the exhaust port 7a as shown in the drawing of FIG. 6A, and larger than that of the muffler 6 in the present exemplary embodiment.

A part of the downstream side portion of the intermediate portion 62 has a substantially horizontal shape parallel to the axis L of the exhaust gas sampling unit 10 and forms an insertion portion 62b to be inserted inside the upstream side portion of the tapered surface 12.

The insertion portion 62b forms a concentric gap with the tapered surface 12 having a tapered shape. On the upstream side, the gap communicates with a space that is on the upstream side of the sampling port 11 and on the downstream side of the expanded portion 62a, whereas on the downstream side, the gap communicates with the inner space on the downstream side of the tapered surface 12 from the opening 63 to thereby form the leakage passage 15 when exhaust gas leaks out as shown by the arrow D.

Inside the leakage passage 15, the inside temperature sensor 52 is disposed in the vicinity of the opening edge portion 14 of the sampling port 11, so that when the exhaust gas leaks as indicated by the arrow D, it is ensured that the leaking exhaust gas passes over the inside temperature sensor 52.

The outside temperature sensor 51 paired with the inside temperature sensor 52 is provided on the outer peripheral surface of the exhaust gas sampling unit 10 which is in the vicinity of the opening edge portion 14 of the sampling port 11 (for convenience sake, only one pair is illustrated as an example). The mounting position of the sensor 51 is lower than the large diameter opening 61 so that the traveling wind (arrow A) passing through the outer peripheral surface passes through the outside temperature sensor 51. However, the upstream side expanded portion 62a including the large diameter opening 61 is positioned so as to cover the upstream side opening of the leakage passage 15 making it less likely for this traveling wind (arrow A) to enter the leakage passage 15, whereby the inside temperature sensor 52 is not cooled.

Almost all the outside air (arrow B) entering the exhaust gas sampling unit 10 passes through the inside of the thermal insulating funnel 60. Therefore, the thermal insulating funnel 60 separates the leakage passage 15 from the traveling air (arrow A) on the outer periphery and the inner peripheral air (arrow B).

As shown in an enlarged cross-sectional view in FIG. 6B, the material of the thermal insulating funnel 60 is constituted of a rigid external metal layer 64 for maintaining the shape, a heat insulating material layer 65 located over the inside of the layer 64 and made of a sponge-like resin such as urethane foam, and an inner metal layer 66 such as an aluminum film covering the inner surface of the layer 65.

With this layered structure, it is possible to reliably insulate the leakage passage 15 from the exhaust gas (arrow C) flowing in the thermal insulating funnel 60, prevent adverse effects on the accuracy of the leakage detection caused by erroneous detection of the temperature of the exhaust gas by the inside temperature sensor 52, and detect the leak accurately, thereby enhancing reliability.

As described above, with the thermal insulating funnel 60 inserted inside the exhaust gas sampling unit 10, the exhaust gas enters the leakage passage 15 only when the exhaust gas leaks out as shown by the arrow D and the inside temperature sensor 52 is capable of reliably detecting this. Also, since the traveling wind (arrow A) passing through the outer peripheral surface cannot easily enter into the leakage passage 15 because of the expanded portion 62a, the influence of the traveling wind (arrow A) passing on the outer peripheral surface is avoided, and accurate temperature detection is made possible.

It is to be noted that illustrated as a cross section perpendicular to the axis of the exhaust gas sampling unit 10 in FIG. 6C is an elastic tube 80 interposed in the leakage passage 15 which is the concentric gap formed between the insertion portion 62b and the tapered surface 12 of the exhaust gas sampling unit 10 in the vicinity of the downstream end portion of the thermal insulating funnel 60. The elastic tube 80 has a hollow cylindrical shape made of a material rich in elasticity, and a plurality of the elastic tubes 80 (in this example there are four) are arranged at equal intervals in the circumferential direction such that the central axis direction of each hollow portion thereof is substantially parallel to the central axis L of the exhaust gas sampling unit 10.

The elastic tube 80 of this example is made of a silicon tube having elasticity and heat resistance. Disposition of this elastic tube 80 in the vicinity of the downstream side end portion of the thermal insulating funnel 60 makes it possible to suppress the vibration transmission to the thermal insulating funnel 60 while keeping a constant distance between the exhaust gas sampling unit 10 and the thermal insulating funnel 60 even if the exhaust gas sampling unit 10 vibrates, and the leakage passage 15 is thus kept constant. In addition, given that the hollow portion of the elastic tube 80 allows the exhaust gas to pass therethrough without disturbance to the flow of the exhaust gas, accurate measurement of the exhaust gas is made possible.

Next, a third exemplary embodiment will be described with reference to FIGS. 7 to 9.

In this embodiment, a filter 70 is disposed between the sampling port 11 and the exhaust port 7a.

Figure 7:
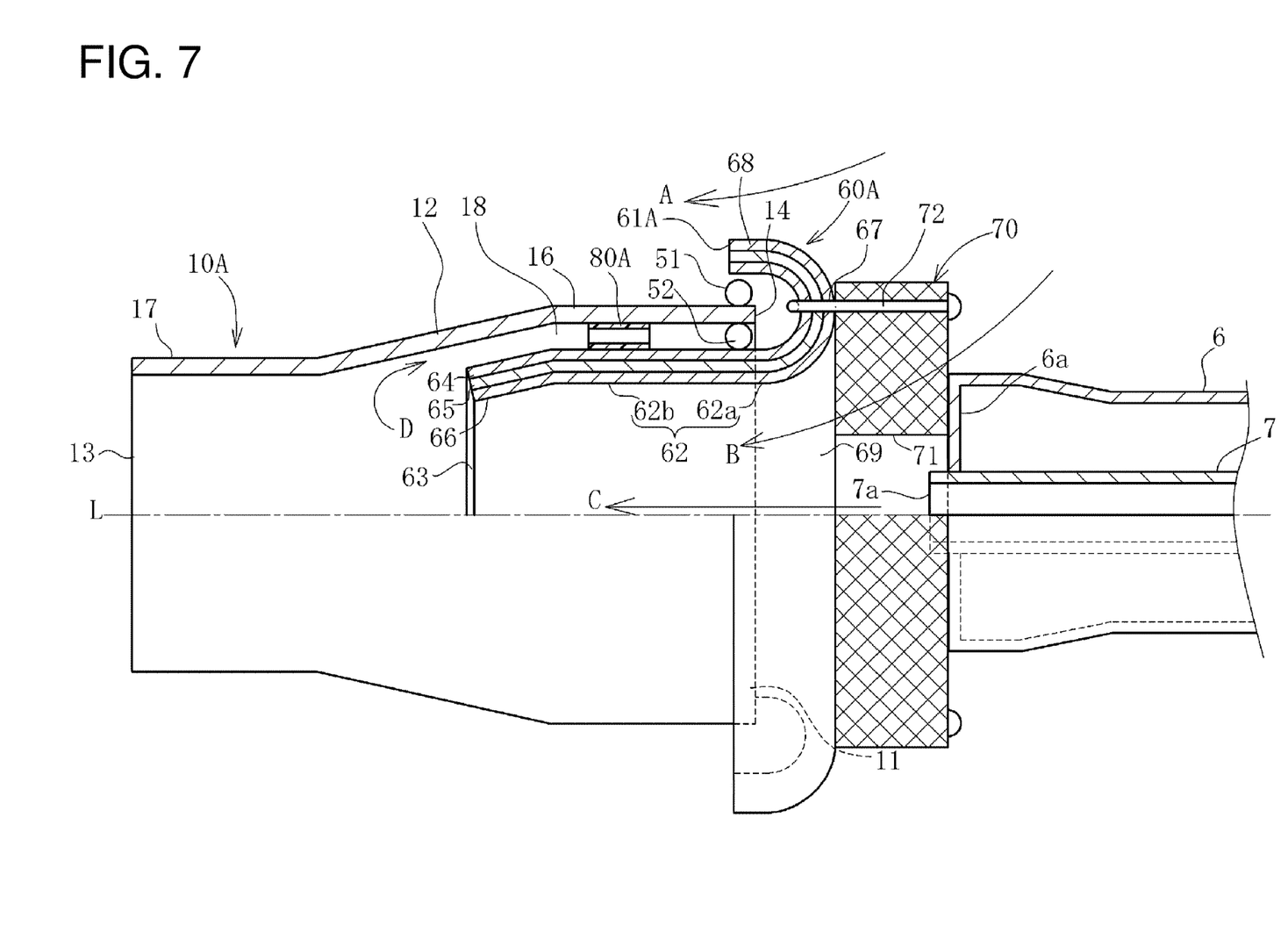
FIG. 7 is a cross-sectional view of a part mainly composed of an exhaust gas sampling unit according to a third exemplary embodiment.

FIG. 7 is a half cross-sectional view taken along the axial direction of the exhaust gas sampling unit 10 and the thermal insulating funnel 60 in a state in which the exhaust port 7a is connected via the filter 70 to an exhaust gas sampling unit 10A and a thermal insulating funnel 60A having slightly different shapes from those in the previous embodiments. However, the exhaust gas sampling unit and the thermal insulating funnel of the preceding embodiments may be freely used as the exhaust gas sampling unit 10A and the thermal insulating funnel 60A of this embodiment.

The exhaust gas sampling unit 10A has straight portions 16 and 17 which are substantially parallel to the axis L at the upstream end portion and the downstream end portion respectively. The upstream side end portion of the straight portion 16 on the upstream side forms the sampling port 11, and the outside temperature sensor 51 and the inside temperature sensor 52 are arranged in a pair inside and outside the vicinity thereof (for convenience sake, only one pair is illustrated).

The thermal insulating funnel 60A is provided with a curved portion 67 that extends backwards in a substantially semicircular arc shape in a radially outward direction at the upstream end portion. A distal end 61A of the curved portion 67 is larger in diameter than the opening edge 14 of the sampling port 11 and a turned portion 68 on the distal end 61A side overlaps the straight portion 16 with a space therebetween. The distal end 61A is positioned downstream than the sampling port 11, and the opening edge portion 14 of the sampling port 11 is surrounded by the curved portion 67 with a space therebetween.

The intermediate portion 62 includes the expanded portion 62a and the insertion portion 62b. The expanded portion 62a extends to the upstream side from the sampling port 11 and continues to the curved portion 67 while curving outward. The insertion portion 62b is inserted into the exhaust gas sampling unit 10A and has a straight portion parallel to the straight portion 16 and a tapered portion parallel to the tapered portion 12. The downstream end of the tapered portion serves as a downstream opening 63.

A gap is formed concentrically between the intermediate portion 62, the tapered portion 12 and the straight portion 16, and this gap serves as a leakage passage 18. The leakage passage 18 is covered by the curved portion 67 as viewed in the axial direction. Further, in the leakage passage 18, an elastic tube 80A similar to that in the previous embodiment is interposed on the downstream side of the straight portion of the insertion portion 62b. However, the elastic tube 80A is disposed between the straight portions at the inner and outer sides, and therefore has a simple shape in which the diameter is constant in the length direction.

Each of the outside temperature sensor 51 and inside temperature sensor 52, constituting a pair, is disposed inside the concave structure of the curved portion 67 having a substantially semi-arc shape cross section so that the upstream side of each sensor is covered by the curved portion 67. With the configuration, the traveling wind (arrow A) passing on the outer peripheral surface and the outside air (arrow B) and exhaust gas (arrow C) flowing inside the insulating funnel 60A are less likely to enter the leakage passage 18. When the exhaust gas leaks, it enters the leakage passage 18 as indicated by the arrow D, and the temperature of the exhaust gas (arrow D) can thus be accurately detected.

An upstream side opening 69 of the thermal insulating funnel 60A is surrounded by the curved portion 67, and the outer peripheral portion of the filter 70 is attached to the most upstream side portion of the curved portion 67 by a fixing member, which in this example is a pin 72.

The pin 72 in this example is inserted from the upstream side to the downstream side with respect to a filter 40, and an enlarged head portion of the pin 72 is brought into contact with the upstream side surface while the distal end side penetrates a through hole formed in the curved portion 67 in advance and folded at the inside of the curved concave structure of the curved portion 67, thereby being easily mounted. Note that the use of a fixing member other than the pin 72 shown in the drawing is optional.

The filter 70 is made of a sponge material having air permeability and elasticity and serves as an air-flow resistance of the outside air taken into the inside of the thermal insulating funnel 60A and is an outside air flow suppressing member for restricting the flow rate of the outside air. The magnitude of the air-flow resistance is appropriately set.

The filter 70 has a ring shape that is substantially donut-shaped, and an exhaust gas passage 71 having a through-hole, the size of which allows the exhaust port 7a to enter, is located in the central portion thereof.

The tail pipe 7 protrudes from a tail cap 6a which closes the rear end of the muffler 6. In the present exemplary embodiment, for the sake of convenience, the upstream side opening 69 of the thermal insulating funnel 60A, the outer periphery of the filter 70, the exhaust gas passage 71, the tail cap 6a of the muffler 6, and the exhaust port 7a are all circular in shape. Each shape is but not limited to a circle, and various shapes are possible as will be described later.

The filter 70 has an outer diameter that is larger than the diameter of the upstream side opening 69 of the thermal insulating funnel 60A, and therefore can cover the opening 69.

The diameter of the exhaust gas passage 71 is larger than the diameter of the exhaust port 7a but smaller than the diameter of the tail cap 6a. The exhaust port 7a can be inserted into the exhaust gas passage 71.

Therefore, by inserting the exhaust port 7a into the exhaust gas passage 71 and having the tail cap 6a of the muffler 6 pressed by the filter 70, the space between the thermal insulating funnel 60A and the tail cap 6a is closed by the filter 70.

However, since the filter 70 has air permeability, outside air can be taken into the thermal insulating funnel 60A from the periphery of the exhaust port 7a through the filter 70 as indicated by arrow B. Given this configuration, the flow rate of the outside air taken into the exhaust gas sampling unit 10A can be limited.

This will be described with reference to FIG. 8.

Figure 8A:
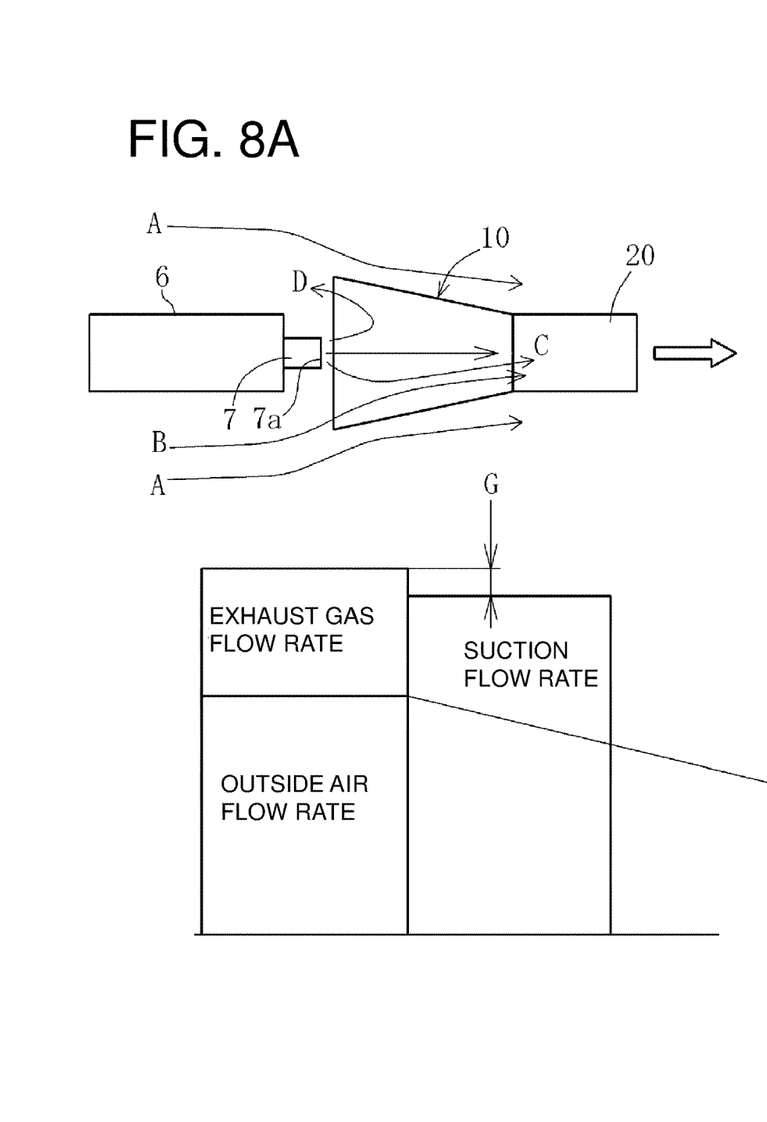
FIG. 8A shows a state without using a filter.
Figure 8B:
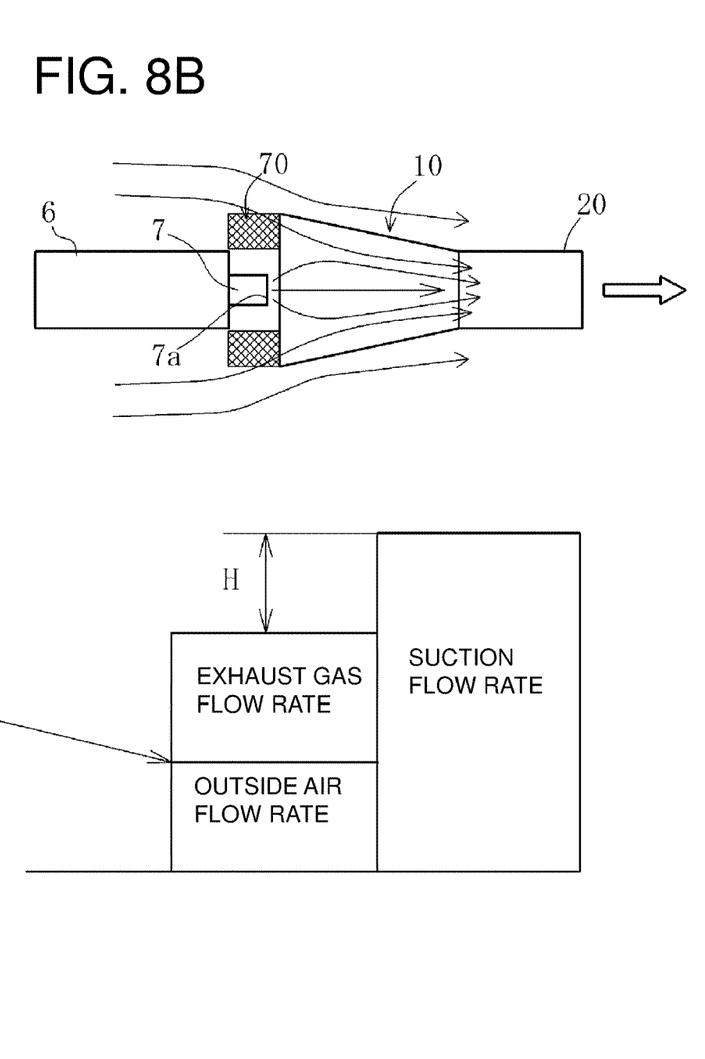
FIG. 8B shows a state using a filter.

Illustrated side by side, FIG. 8A shows a state without using a filter and FIG. 8B shows a state using a filter. The graph under the diagram illustrates the exhaust gas flow rate taken into the exhaust gas sampling unit 10 and the flow rate of the outside air and the suction flow rate aspirated by the suction blower 24 (FIG. 1). Note that the exhaust gas sampling unit 10 of the first exemplary embodiment is used and the leak detection mechanism 50 is omitted in this embodiment.

First, in FIG. 8A, in the absence of the filter, when the total inflow flow rate which is the sum of the flow rate of the exhaust gas and the flow rate of the outside air becomes larger than the suction flow rate aspirated by the suction blower 24, an excessive flow rate G which cannot be aspirated occurs. Only the exhaust gas of this excessive flow rate is bounced back from the exhaust gas sampling unit 10 to the upstream side as indicated by the arrow D and leaks out from the sampling port 11.

On the other hand, as shown in FIG. 8B, when the filter 70 is used, the filter 70 suppresses the flow rate of the outside air entering the exhaust gas sampling unit 10. Therefore, when the flow rate of the exhaust gas and the suction flow rate are constant (FIG. 8A), the total inflow flow entering the exhaust gas sampling unit 10 can be made smaller in the amount of the adjustment flow rate H than the suction flow rate. As a result, it is possible to aspirate the whole amount.

With this configuration in which the filter 70 is used, leakage of the exhaust gas can be prevented by simply adjusting the flow rate of the outside air entering the exhaust gas sampling unit 10. Further, this filter 70 can be combined with the thermal insulating funnel 60 of the second exemplary embodiment. In this case, the attachment of the filter 70 becomes easy with the expanded portion 62a that is configured to have a flange shape extending in the axis orthogonal direction.

Furthermore, the regulation of the flow rate of the outside air entering the exhaust gas sampling unit 10 by the filter 70 is performed by adjusting the air-flow resistance of the filter 70. The air-flow resistance can be freely adjusted depending on the material, thickness, degree of communication, etc. of the filter 70.

Moreover, the filter 70 is made of a resilient sponge-like material. Therefore, the muffler, even if it is irregularly shaped for example, can be brought into close contact with the filter 70 due to the elastic deformation, thereby tightly sealing the gap between the sampling port 11 of the exhaust gas sampling unit 10 and the exhaust port 7a.

In addition, the connection of the filter 70 to the periphery of the exhaust port 7a and the sampling port 11 is facilitated.

It is to be noted that the present invention is not limited to the above embodiments and various modifications thereof can made. For example, leak detection can be carried out by using only the measured temperature of the outer sensor or the inner sensor without using the leakage detection method that is based on the temperature difference between the inside and the outside sensors. In this case, if a threshold value with respect to measured temperatures is set in advance, the occurrence of leakage can be detected through a rapid rise in temperature. Although this method is less accurate than the one based on the temperature difference between the inside and the outside sensors, leakage detection becomes possible by measuring the temperature. Moreover, compared with the conventional concentration analysis, the temperature measurement is easier to measure and the device is simple and inexpensive.

REFERENCE SIGNS LIST

1 . . . Open Emission Analysis System
2 . . . motorcycle
4 . . . exhaust pipe
6 . . . muffler
7 . . . tail pipe
7a . . . exhaust port
10 . . . exhaust gas sampling unit
11 . . . sampling port
14 . . . opening edge portion of sampling port
15, 18 . . . leakage passage
50 . . . leak detection mechanism
51 . . . outside sensor
52 . . . inside sensor
53, 54 . . . signal line
55 . . . temperature measuring unit
60, 60A . . . thermal insulating funnel (inner insertion tube)
62a . . . expanded portion
67 . . . curved portion
70 . . . filter
71 . . . exhaust gas passage

The invention claimed is:

1. A leak detection method for open emission analysis, comprising steps of:
   taking in exhaust gas discharged from an exhaust port, together with ambient outside air, using an exhaust gas sampling unit;
   analyzing the collected exhaust gas; and
   performing temperature measuring in the vicinity of a sampling port of the exhaust gas sampling unit to detect a leakage of exhaust gas from the sampling port, the temperature measurement being performed in the vicinity of the sampling port at both inside and outside positions of the sampling port,
   wherein a leakage of exhaust gas is detected when a temperature difference between inside and outside temperatures exceeds a predetermined threshold value.

2. The leak detection method for open emission analysis according to claim 1, wherein
   the temperature measurement is performed at a plurality of locations spaced apart from each other by a predetermined interval in a circumferential direction of the sampling port.

3. An open emission analysis device configured to detect exhaust gas leaks, said device comprising:
   an exhaust gas sampling unit for taking in exhaust gas discharged from an exhaust port together with ambient outside air; and
   a concentration analysis unit for analyzing the sampled gas;
   wherein:
   the exhaust gas sampling unit has a sampling port that is larger than the exhaust port, and
   a temperature detecting unit is arranged in the vicinity of the sampling port,
   the temperature detecting unit includes a pair of temperature sensors, including an outside temperature sensor for detecting an outside temperature on an outer peripheral surface of the exhaust gas sampling unit, and an inside temperature sensor for detecting a temperature on an inner peripheral surface of the exhaust gas sampling unit, and
   the device further comprises a temperature measuring unit for detecting a temperature difference between the respective detected temperatures of the inside and outside temperature detecting units, and for detecting a leakage of exhaust gas when a temperature difference between inside and outside temperatures exceeds a predetermined threshold value.

4. The open emission analysis device according to claim 3, wherein
   the device includes a plurality of the temperature detecting units arranged at a plurality of locations spaced apart from each other by a predetermined interval in the circumferential direction of the sampling port.

5. The open emission analysis device according to claim 3, wherein:
the exhaust gas sampling unit is a hollow tubular member, and has an inner insertion tube with a downstream side portion thereof being inserted to the exhaust gas sampling unit,
the inner insertion tube is open at both ends thereof,
the inner insertion tube forms a gap with the inner peripheral surface of the exhaust gas sampling unit to form a leakage passage through which leaked exhaust gas passes; and
the temperature detecting unit is disposed in the leakage passage.

6. The open emission analysis device according to claim 5, wherein
the inner insertion tube has an upstream side portion extending upstream from the sampling port of the exhaust gas sampling unit and has an expanded portion which expands radially outward, the expanded portion has a distal end that is located radially outward from the sampling port and covers the upstream side of the leakage passage as viewed in the axial direction.

7. The open emission analysis device according to claim 5, wherein
the inner insertion tube in the gap has an upstream side portion extending upstream from the sampling port of the exhaust gas sampling unit, and includes a curved portion extending radially outwards so as to surround the edge portion of the sampling port and provide a concave structure, and
an opening edge portion of the sampling port is located inside of the concave structure of the curved portion.

8. The open emission analysis device according to claim 5, wherein at least a portion of the inner insertion tube is made of a heat insulating material.

9. The open emission analysis device according to claim 5, wherein an upstream side opening of the inner insertion tube is connected to the exhaust port via a filter having air permeability.

10. The open emission analysis device according to claim 9, wherein the filter is made of an elastic member.

* * * * *